United States Patent
Tu et al.

(12) 
(10) Patent No.: US 6,432,870 B1
(45) Date of Patent: Aug. 13, 2002

(54) PROCESS FOR PREPARING METAL OXIDE CATALYST FOR ACRYLIC ACID PRODUCTION

(75) Inventors: Xinlin Tu; Mamoru Takahashi; Hiroshi Niizuma, all of Aichi (JP)

(73) Assignee: Toagosei Co., Ltd., Tokyo (JP)

( * ) Notice: Subject to any disclaimer, the term of this patent is extended or adjusted under 35 U.S.C. 154(b) by 0 days.

(21) Appl. No.: 09/576,770

(22) Filed: May 24, 2000

(30) Foreign Application Priority Data

May 25, 1999 (JP) .......................................... 11-144429
Jun. 17, 1999 (JP) .......................................... 11-171636

(51) Int. Cl.$^7$ ............................................... B01J 23/00
(52) U.S. Cl. ..................... 502/305; 502/306; 502/307; 502/308; 502/310; 502/311; 502/312; 502/313; 502/314; 502/317; 502/318; 502/322; 502/323
(58) Field of Search .................. 502/107, 305–307, 502/308, 310, 311, 312, 313, 314, 317, 318, 322, 323, 327, 330, 331, 332, 344, 345, 346, 347, 348, 349, 352, 354, 355, 527.15, 527.12; 423/22, 23, 61, 62, 87, 89, 111, 593

(56) References Cited

U.S. PATENT DOCUMENTS

| | | | | |
|---|---|---|---|---|
| 3,903,149 A | * | 9/1975 | Kadowaki et al. | 260/530 N |
| 4,021,427 A | * | 5/1977 | Dolhyj et al. | 260/346.8 A |
| 4,092,354 A | * | 5/1978 | Shiraishi et al. | 260/530 |
| 4,115,441 A | * | 9/1978 | Shaw et al. | 562/534 |
| 4,212,766 A | * | 7/1980 | Brazdil et al. | 252/432 |
| 4,256,914 A | * | 3/1981 | Umemura et al. | 562/535 |
| 4,259,211 A | * | 3/1981 | Krabetz et al. | 252/443 |
| 4,271,040 A | * | 6/1981 | Khoobiar | 252/437 |
| 4,469,810 A | * | 9/1984 | Kato et al. | 502/209 |
| 4,487,962 A | * | 12/1984 | Krabetz et al. | 562/534 |
| 4,547,588 A | * | 10/1985 | Khoobiar | 562/535 |
| 4,804,778 A | * | 2/1989 | Oh-Kita et al. | 562/534 |
| 4,892,856 A | * | 1/1990 | Kawajiri et al. | 502/247 |
| 5,198,580 A | * | 3/1993 | Bartek et al. | 562/542 |
| 5,380,933 A | * | 1/1995 | Ushikubo et al. | 562/549 |
| 5,449,821 A | * | 9/1995 | Neumann et al. | 562/546 |
| 5,493,052 A | * | 2/1996 | Tenten et al. | 562/534 |
| 5,498,588 A | * | 3/1996 | Brazdil et al. | 502/353 |
| 5,521,137 A | * | 5/1996 | Martin et al. | 502/311 |
| 5,569,636 A | * | 10/1996 | Martin et al. | 502/311 |
| 5,808,143 A | * | 9/1998 | Karrer et al. | 562/407 |
| 5,910,608 A | * | 6/1999 | Tenten et al. | 562/532 |
| 5,994,580 A | * | 11/1999 | Takahashi et al. | 562/549 |
| 6,060,422 A | * | 5/2000 | Takahashi et al. | 502/312 |
| 6,114,278 A | * | 9/2000 | Karim et al. | 502/312 |
| 6,180,825 B1 | * | 1/2001 | Lin et al. | 562/549 |
| 6,239,325 B1 | * | 5/2001 | Kishimoto et al. | 585/658 |

* cited by examiner

*Primary Examiner*—Steven P. Griffin
*Assistant Examiner*—Cam N. Nguyen
(74) *Attorney, Agent, or Firm*—Sughrue Mion, PLLC

(57) ABSTRACT

A process for preparing a metal oxide catalyst for acrylic acid production which comprises calcining a metal compound mixture at 400° C. or higher to prepare a metal oxide powder comprising Mo, V, Sb, and at least one element selected from the group consisting of Nb and Ta, and supporting a compound comprising at least one element selected from the group consisting of Sb, Tl, Se, As, Pb, Sn, Ag, Cu, Ru, and Rh on the metal oxide powder, and a process for producing acrylic acid by gas phase oxidation of propane using the catalyst.

2 Claims, No Drawings

PROCESS FOR PREPARING METAL OXIDE CATALYST FOR ACRYLIC ACID PRODUCTION

FIELD OF THE INVENTION

This invention relates to a process for preparing a metal oxide catalyst for producing acrylic acid by gas phase catalytic oxidation of propane and a process for producing acrylic acid using the catalyst.

BACKGROUND OF THE INVENTION

Acrylic acid has been produced by a two-stage process comprising catalytic oxidation of propylene with oxygen to once prepare acrolein, which is then catalytically oxidized with oxygen. A one-stage process for acrylic acid synthesis comprising oxidation of propane has been studied as a promising process that would greatly reduce the production cost compared with the two-stage process.

For example, JP-A-9-316023 proposes a four-component metal oxide catalyst for the one-stage process, which is composed of Mo, V, Sb, and a metal selected from Nb, Ta, W, Ti, Cr, Fe, etc. A four-component metal oxide catalyst comprising similar metals is also described in JP-A-10-45664.

JP-A-10-120617 discloses a metal oxide catalyst superior to the above-described four-component systems in conversion and selectivity in the acrylic acid synthesis, which is composed basically of five components including the four components according to JP-A-10-316023 supra which are impregnated with a solution containing an additional component selected from As, P or an alkali metal. According to the disclosure, one-stage oxidation of propane in the presence of the five-component metal oxide catalyst achieves an acrylic acid yield of about 20 to 25%.

JP-A-10-28862 proposes a metal oxide catalyst, which is designed chiefly for catalytic oxidation reaction between alkane and ammonia to synthesize nitrile. This catalyst comprises the four-component metal oxide system of JP-A-10-45664 supra which further has supported thereon at least one element selected from Mo, W, Zr, Cr, Ti, Nb, Ta, Fe, P, Si, an alkali metal, an alkaline earth metal, etc.

SUMMARY OF THE INVENTION

The present invention provides a process for preparing a metal oxide catalyst for acrylic acid production which comprises calcining a metal compound mixture at 400° C. or higher to prepare a metal oxide powder comprising Mo, V, Sb and at least one element selected from the group consisting of Nb and Ta, and supporting a compound comprising at least one element selected from the group consisting of Sb, Tl, Se, As, Pb, Sn, Ag, Cu, Ru and Rh on the metal oxide powder; and a process for producing acrylic acid using the catalyst.

The present invention also provides a process for preparing a metal oxide catalyst for acrylic acid production which comprises calcining a metal compound mixture at 400° C. or higher to prepare a metal oxide powder comprising Mo, V, Sb, at least one element selected from the group consisting of Nb and Ta, and at least one element selected from the group consisting of Ag, Zn, Sn, Pb, As, Cu, Tl and Se, and supporting a compound comprising at least one element selected from the group consisting of Sb, Tl, Se, As, Pb, Sn, Ag, Cu, Ru and Rh, Na, and K on the metal oxide powder; and a process for producing acrylic acid using the catalyst.

According to the present invention, a catalyst for producing acrylic acid by gas phase oxidation of propane in a high yield is provided.

DETAILED DESCRIPTION OF THE INVENTION

The metal oxide on which a compound comprising at least one element selected from the group consisting of Sb, Tl, Se, As, Pb, Sn, Ag, Cu, Ru and Rh (hereinafter referred to as element X) is to be supported is a metal oxide composed of Mo, V, Sb, at least one of Nb and Ta (hereinafter referred to as element A), and oxygen (hereinafter referred to as "metal oxide (a)"). The metal oxide on which a compound comprising at least one element selected from the group consisting of the element X, Na, and K is to be supported is a metal oxide composed of Mo, V, Sb, A, at least one element selected from the group consisting of Ag, Zn, Sn, Pb, As, Cu, Tl, and Se (hereinafter referred to as element B), and oxygen (hereinafter referred to as metal oxide (ab)).

The metal oxide (a) is preferably prepared by a process comprising a first step in which a pentavalent vanadium compound (e.g., ammonium metavanadate or vanadium pentoxide) and a trivalent antimony compound (e.g., antimony trioxide or antimony acetate) are allowed to react at 70° C. or higher in an aqueous medium in the presence of a hexavalent molybdenum compound (e.g., ammonium molybdate, molybdenum oxide or molybdic acid), a second step in which the resulting reaction product is uniformly mixed with a compound comprising the element A (hereinafter "metal A compound"), and a third step in which the resulting mixture is calcined.

The calcining temperature should be higher than 400° C. For example, calcination usually completes at 450° to 700° C. for 1 to 3 hours.

The metal A compound includes niobium oxide, niobic acid, tantalum oxide, and tantalic acid.

The metal oxide (a), when represented by a compositional formula:

$$MoV_gSb_hA_i \quad (1)$$

preferably has such an atomic ratio that g and h are each 0.01 to 1.5 at h/g=0.3 to 1; and i is 0.01 to 3.0. If h/g is smaller than 0.3, the selectivity to acrylic acid is low. If i is smaller than 0.001, the catalyst is prone to deterioration. If i exceeds 3.0, the catalyst has low activity, resulting in a low conversion of propane.

The metal oxide (ab) can be obtained in the same manner as for the metal oxide (a), except that a compound containing the element B (hereinafter "metal B compound") is used in combination with the hexavalent molybdenum compound in the first step or that the metal B compound is added together with the metal A compound in the second step.

The metal B compound includes silver compounds, such as silver nitrate, silver acetate and silver carbonate; zinc compounds, such as zinc nitrate and zinc oxide; tin compounds, such as stannous chloride and stannic chloride; lead compounds, such as lead acetate and lead chloride; arsenic compounds, such as arsenic trioxide and arsenic oxide; copper compounds, such as copper nitrate, cupric oxide and cuprous oxide; thallium compounds, such as thallous nitrate and thallic nitrate; and selenium compounds, such as selenic acid, selenious acid, and selenic chloride.

The metal oxide (ab), when represented by a compositional formula:

$$MoV_gSb_hA_iB_j \quad (2)$$

preferably has such an atomic ratio that g and h are each 0.01 to 1.5 at h/g=0.3 to 1; i is 0.001 to 3.0; and j is 0.0001 to 0.05. If h/g is less than 0.3, the selectivity to acrylic acid is low.

If i is smaller than 0.001, the catalyst is apt to deteriorate. If i exceeds 3.0, the catalyst has low activity, and the propane conversion is poor. If j is smaller than 0.0001, the effect of addition of the element B is insubstantial. If j is greater than 0.05, the yield of acrylic acid is reduced.

In the preparation of the metal oxide (a) or the metal oxide (ab), the reaction of the first step is preferably carried out at around the boiling point of the aqueous medium for 10 to 30 hours.

In order to accelerate the redox reaction among $Sb^{+3}$, $V_{+5}$ and $Mo^{+6}$ in the first step, it is a preferred embodiment that oxygen gas is blown into the reaction system, or hydrogen peroxide is dropped in the reaction system after the redox reaction has proceeded to some extent.

Oxygen-containing gas, such as air, can be used in place of oxygen gas. A preferred oxygen concentration in the oxygen-containing gas is at least 0.5% by volume, particularly 1 to 20% by volume, especially 2 to 15% by volume. Introduction of oxygen-containing gas is preferably continued for 4 hours or longer.

In dropping hydrogen peroxide, aqueous hydrogen peroxide having a concentration of 0.01 to 35% by weight is preferred. Hydrogen peroxide is preferably added in an amount of 0.2 to 1.2 mol per mole of Sb. The reaction mixture to which hydrogen peroxide is added is preferably kept at 80 to 100° C. Dropwise addition of hydrogen peroxide may be completed in a short period of time or over a long period of time.

In the second step, the metal A compound (i.e., an Nb compound and/or a Ta compound) is added to the reaction mixture containing Mo, V and Sb either as is obtained in the form of a dispersion or after solidified by evaporation. The Nb compound or Ta compound is preferably added in the form of an aqueous solution of its oxalate. In this case, it is preferred for the reaction mixture to which the metal compound A is added to contain ammonium ions. Ammonia or aqueous ammonia solution is preferred as an ammonium ion source. The ammonium ions and oxalate ions are preferably added in amounts of 2 to 7 mol and 4 to 12 mol, respectively, per mole of the element A.

The mixture obtained is evaporated to dryness and then preferably further calcined at 450 to 700° C. for 1 to 3 hours. The contents of the constituent metal elements of the resulting metal oxide (a) or (ab) can be confirmed by X-ray fluorescence analysis.

The metal oxide (a) or (ab) is dry or wet ground to powder of appropriate size, preferably 20 μm or smaller, particularly 5 μm or smaller. Grinding can be carried out by means of a mortar, a ball mill, and the like. In wet grinding, water or an alcohol is used as a grinding aid.

In the present invention, a compound comprising the element X (hereinafter "metal X compound") is supported on the metal oxide (a), or a compound comprising the element X, Na or K is supported on the metal oxide (ab). Of the metal elements X, Na and K, preferred are K, Na, Sb, and Tl, still preferred are K and Na, particularly preferred is K.

The atomic ratio of the element X, Na or K supported on the metal oxide (a) or (ab) to Mo of the metal oxide is preferably 0.001 to 0.3, particularly 0.002 to 0.1. If the atomic ratio is less than 0.001, the yield of acrylic acid is low. If it exceeds 0.3, the element X, Na or K will cover the active sites of the supporting oxide, resulting in a reduced conversion of propane.

The metal X compound includes antimony compounds, such as antimony trioxide and antimony acetate; thallium compounds, such as thallous nitrate and thallic nitrate; selenium compounds, such as selenic acid, selenious acid, and selenic chloride; arsenic compounds, such as arsenic trioxide and arsenic oxide; lead compounds, such as lead nitrate, lead acetate, and lead chloride; tin compounds, such as stannous chloride and stannic chloride; silver compounds, such as silver nitrate, silver acetate, and silver carbonate; copper compounds, such as copper nitrate, cupric oxide, and cuprous oxide; ruthenium compounds, such as ruthenium chloride; and rhodium compounds, such as rhodium nitrate, rhodium acetate, and rhodium chloride.

The Na or K compound includes sodium carbonate, sodium hydrogencarbonate, sodium hydroxide, sodium nitrate, sodium oxide, potassium hydroxide, potassium hydrogencarbonate, potassium nitrate, potassium oxide, and so forth.

The metal X compound, Na compound or K compound is preferably supported on the metal oxide (a) or metal oxide (ab) by a method comprising mixing the oxide powder with a solution of the metal X compound, Na compound or K compound in an organic solvent. The metal compound can also be supported on the metal oxide powder by dissolving the metal compound in a solvent to be used in wet grinding of the metal oxide (a) or (ab). A suitable concentration of the metal compound in the solution is 0.1 to 1.0 mol/l. The solution is preferably used in an amount of 20 to 50 parts by weight per 100 parts by weight of the metal oxide (a) or (ab). The metal compound and the metal oxide (a) or (ab) powder are mixed as uniformly as possible by stirring. Thereafter, the solvent is evaporated from the mixture to give a powder of the metal oxide having the metal compound supported thereon.

If desired, the resulting powder may be calcined at 300 to 500° C. for about 1 to 5 hours. In the case where calcination is not carried out, the powder is preferably dried at 100 to 200° C. Calcination is carried out in air, nitrogen gas, etc. A nitrogen atmosphere is preferred. The contents of metals in the resulting metal oxide catalyst can be confirmed by X-ray fluorescence analysis. The resulting metal oxide catalyst can be used either as such or as supported on a carrier having an appropriate particle size, such as silica, alumina, silica alumina or silicon carbide.

The process for producing acrylic acid according to the invention comprises feeding propane and oxygen gas to a reactor and allowing them to react in the presence of the catalyst of the invention. Propane and oxygen may be fed to the reactor through separate lines, or they may be mixed previously before being introduced into the reactor. The oxygen gas includes pure oxygen, air, and pure oxygen or air diluted with steam or carbonic acid gas. In case where air is used, it is preferably fed in an amount 30 times or less, particularly 0.2 to 20 times, the volume of propane. The reaction is preferably carried out at a temperature of from 300 to 600° C., particularly 350 to 500° C., at a space velocity (S.V.) of 300 to 5,000 $hr^{-1}$.

The present invention will now be illustrated in greater detail with reference to Preparation Examples, Examples, and Comparative Examples, but it should be understood that the invention is not construed as being limited thereto. Unless otherwise noted, all the percents are by weight.

Preparation Example 1

Preparation of Metal Oxide (a)-1

In a 300 ml glass-made flask was put 130 ml of distilled water, and 6.15 g of ammonium metavanadate was dissolved therein by stirring under heat. To the solution were added 5.87 g of antimony trioxide and 30.9 g of ammonium molybdate. The mixture was heated under reflux for 16 hours while stirring at 360 rpm in a nitrogen gas atmosphere. After 16 hour-reacting, 40 g of 1.71% aqueous hydrogen peroxide was added dropwise to the reaction mixture over 5 hours while heating with stirring.

The resulting blue colloidal dispersion was cooled to room temperature, and a solution (room temperature) of 8.82 g of oxalic acid, 2.33 g of niobic acid, and 3.0 g of 28% aqueous ammonia in 75 ml of distilled water was added thereto, followed by vigorously stirring for 30 minutes. Then, the water content was gradually evaporated to dryness at a final temperature of 120° C.

The residual solid was calcined in air at 280° C. for 5 hours and then in a nitrogen atmosphere at 580° C. for 2 hours to obtain metal oxide (a)-1. Metal oxide (a)-1 had an Mo/V/Sb/Nb atomic ratio of 1.0/0.3/0.23/0.08.

Preparation Example 2
Preparation of Metal Oxide (ab)-1

Metal oxide (ab)-1 was prepared in the same manner as in Preparation Example 1, except for adding 0.14 g of thallium (I) nitrate in combination with the antimony trioxide and the ammonium molybdenum and that the addition of hydrogen peroxide was performed by adding dropwise 40 g of 1.54% aqueous hydrogen peroxide over a 5 minute period. Metal oxide (ab)-1 was found to have an Mo/V/Sb/Nb/Tl atomic ratio of 1.0/0.3/0.23/0.08/0.003.

Preparation Example 3
Preparation of Metal Oxide (ab)-2

Metal oxide (ab)-2 was prepared in the same manner as in Preparation Example 2, except for replacing 0.14 g of thallium (I) nitrate with 0.317 g of a 82% selenium solution. Metal oxide (ab) -2 had an Mo/V/Sb/Nb/Se atomic ratio of 1.0/0.3/0.23/0.08/0.008.

EXAMPLE 1

A solution of 0.169 g of thallium (I) nitrate in 7 g of distilled water was added to 10 g of the metal oxide (a) -1 obtained in Preparation Example 1 and thoroughly mixed. The mixture was dried at 120° C. for 1 hour to obtain a metal oxide catalyst. X-ray fluorescence analysis on the catalyst revealed that the Mo/V/Sb/Nb/Tl (impregnant) atomic ratio was 1.0/0.3/0.23/0.08/0.014.

The catalyst was tabletted, crushed and sieved to 16 to 30 mesh, and 1.5 ml of the particle was packed in a quartz reaction tube of 10 mm in diameter. The reaction tube was heated to 390° C., and a mixed gas of 4.5 vol % propane, 7.1 vol % oxygen, 25 vol % nitrogen, and 63.4 vol % steam was fed therein at an S.V. of 2,380 hr−1 (contact time: 2 sec) to synthesize acrylic acid. The conversion of propane was 54.0%, the selectivity to acrylic acid was 63.5%, and the yield of acrylic acid was 34.3%.

The conversion, selectivity, and yield were calculated on a molar basis according to the following equations (hereinafter the same).

Conversion (%)=(fed propane−unreacted propane)/fed propane

Selectivity (%)=produced acrylic acid/(fed propane−unreacted propane)

Yield (%)=conversion×selectivity

EXAMPLE 2

A metal oxide catalyst was prepared in the same manner as in Example 1, except for replacing the thallium (I) nitrate aqueous solution with a mixture of 0.080 g of antimony trioxide, 7.0 g of distilled water, and 0.60 g of 30% hydrochloric acid. The resulting catalyst had an atomic ratio of Mo/V/Sb/Nb/Sb (impregnant) of 1.0/0.3/0.23/0.08/0.013.

Acrylic acid was synthesized by using the resulting catalyst in the same manner as in Example 1.

EXAMPLE 3

A metal oxide catalyst was prepared in the same manner as in Example 1, except for replacing the thallium (I) nitrate aqueous solution with a solution of 0.210 g of lead nitrate in 7.0 g of distilled water. The resulting catalyst had an atomic ratio of Mo/V/Sb/Nb/Pb (impregnant) of 1.0/0.3/0.23/0.08/0.014.

Acrylic acid was synthesized by using the resulting catalyst in the same manner as in Example 1.

EXAMPLE 4

A metal oxide catalyst was prepared in the same manner as in Example 2, except for replacing the metal oxide (a)-1 with metal oxide (ab)-1 prepared in Preparation Example 2. The resulting catalyst had an atomic ratio of Mo/V/Sb/Nb/Tl/Sb (impregnant) of 1.0/0.3/0.23/0.08/0.003/0.013.

Acrylic acid was synthesized by using the resulting catalyst in the same manner as in Example 1.

Comparative Examples 1 and 2

Acrylic acid was synthesized in the same manner as in Example 1, except for using metal oxide (a)-1 (Comparative Example 1) or metal oxide (ab)-l (Comparative Example 2) as a catalyst.

EXAMPLE 5

Ten grams of metal oxide (ab)-l prepared in Preparation Example 2 and a solution of 0.034 g of sodium carbonate in 7 g of water were thoroughly mixed and dried at 120° C. for 1 hour to obtain a metal oxide catalyst. As a result of X-ray fluorescence analysis, the catalyst had an Mo/V/Sb/Nb/Tl/Na (impregnant) atomic ratio of 1.0/0.3/0.23/0.08/0.003/0.013.

Acrylic acid was synthesized by using the resulting talyst in the same manner as in Example 1.

EXAMPLE 6

A metal oxide catalyst was prepared in the same manner as in Example 5, except that 10 g of metal oxide (ab)-2 prepared in Preparation Example 3 and a solution of 0.063 g of potassium hydrogencarbonate in 7 g of distilled water were used. The atomic tio of the resulting catalyst was Mo/V/Sb/Nb/Se/K (impregnant) =1.0/0.3/0.23/0.08/0.008/0.014.

Acrylic acid was synthesized by using the resulting catalyst in the same manner as in Example 1.

The reaction results of the acrylic acid synthesis in Examples 1 to 6 and Comparative Examples 1 and 2 are shown in Table 1 below.

TABLE 1

|  | Conversion (%) | Selectivity (%) | Yield (%) |
| --- | --- | --- | --- |
| Example 1 | 54.0 | 63.5 | 34.3 |
| Example 2 | 56.0 | 54.3 | 30.4 |
| Example 3 | 63.2 | 45.2 | 28.6 |
| Example 4 | 56.6 | 54.0 | 30.6 |
| Example 5 | 59.5 | 55.2 | 32.8 |
| Example 6 | 59.6 | 57.8 | 34.4 |

TABLE 1-continued

|  | Conversion (%) | Selectivity (%) | Yield (%) |
|---|---|---|---|
| Comparative Example 1 | 51.1 | 49.2 | 25.1 |
| Comparative Example 2 | 55.9 | 51.0 | 28.5 |

While the invention has been described in detail and with reference to specific examples thereof, it will be apparent to one skilled in the art that various changes and modifications can be made therein without departing from the spirit and scope thereof.

What is claimed is:

1. A process for preparing a metal oxide catalyst for acrylic acid production which comprises calcining a metal compound mixture at 400° C. or higher to prepare a metal oxide powder comprising Mo, V, Sb, and at least one element selected from the group consisting of Nb and Ta, and supporting a compound comprising at least one element selected from the group consisting of Sb, Tl, Se, As, Pb, Sn, Ru, and Rh on the metal oxide powder.

2. A process for preparing a metal oxide catalyst for acrylic acid production which comprises calcining a metal compound mixture at 400° C. or higher to prepare a metal oxide powder comprising Mo, V, Sb, at least one element selected from the group consisting of Nb and Ta, and at least one element selected from the group consisting of Ag, Zn, Sn, Pb, As, Cu, Tl, and Se, and supporting a compound comprising at least one element selected from the group consisting of Sb, Tl, Se, As, Pb, Sn, Ru, Rh, Na and K on the metal oxide powder.

* * * * *